(12) United States Patent
Zahedi et al.

(10) Patent No.: US 6,517,585 B1
(45) Date of Patent: Feb. 11, 2003

(54) LOWER LIMB PROSTHESIS

(75) Inventors: Mir Saeed Zahedi, Guildford (GB); Andrew John Sykes, Camberley (GB); Stephen Terry Lang, Fareham (GB)

(73) Assignee: Chas. A. Blatchford & Sons Limited, Basingstoke (GB)

( * ) Notice: Subject to any disclaimer, the term of this patent is extended or adjusted under 35 U.S.C. 154(b) by 0 days.

(21) Appl. No.: 09/485,800

(22) PCT Filed: Aug. 13, 1998

(86) PCT No.: PCT/GB98/02438
§ 371 (c)(1),
(2), (4) Date: May 3, 2000

(87) PCT Pub. No.: WO99/08621
PCT Pub. Date: Feb. 25, 1999

(30) Foreign Application Priority Data

Aug. 15, 1997 (GB) .............................................. 9717380
Jun. 26, 1998 (GB) .............................................. 9813904

(51) Int. Cl.[7] ................................ A61F 2/48; A61F 2/64
(52) U.S. Cl. ............................ 623/24; 623/43; 623/45
(58) Field of Search ............................ 623/24, 44, 45, 623/43

(56) References Cited

U.S. PATENT DOCUMENTS

| 4,212,087 A | 7/1980 | Mortensen | 3/1.2 |
|---|---|---|---|
| 5,092,902 A | 3/1992 | Adams et al. | 623/26 |
| 5,405,409 A | 4/1995 | Knoth | 623/44 |
| 5,571,205 A | 11/1996 | James | 623/24 |
| 5,888,212 A * | 3/1999 | Petrofsky et al. | 623/24 |
| 5,893,891 A * | 4/1999 | Zahedi | 623/24 |

FOREIGN PATENT DOCUMENTS

| EP | 0 549 855 A2 | 7/1993 | A61F/2/64 |
|---|---|---|---|
| FR | 2 677 540 | 12/1992 | A61F/2/30 |
| GB | 2 253 791 | 9/1992 | A61F/2/64 |
| WO | WO 92/2226 | 12/1992 | A61F/2/64 |

* cited by examiner

*Primary Examiner*—Bruce Snow
(74) *Attorney, Agent, or Firm*—Hale & Dorr LLP

(57) ABSTRACT

A lower limb prosthesis for an above-knee amputee has an adaptive control system which includes a knee flexion control device arranged to resist flexion at the knee joint both hydraulically and pneumatically by means of a dual piston and cylinder assembly. Sensors arranged to sense knee bending moments and knee flexion angle provide electrical signals which are fed to a processing circuit for automatically adjusting the hydraulic and pneumatic resistance to flexion according to the activity mode of the amputee and, when walking, according to the speed of the cylinder containing hydraulic fluid. The hydraulic resistance to flexion predominates during the stance phase and pneumatic resistance predominates during the swing phase. Provision is made for programmable resistance during level walking, walking on an incline, descending stairs and during a stumble.

55 Claims, 11 Drawing Sheets

Fig.6-1: Select ramp descent mode IF Current normalised force integral > maximum normalised flat force integral + ramp offset + safety offset Fig.6-2: Exit ramp descent mode IF Current normalised force integral < maximum normalised flat force integral

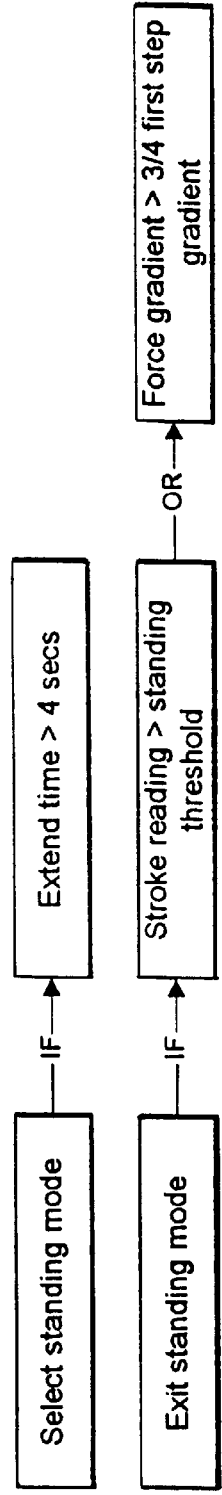

Fig.6-3: Select standing mode IF Extend time > 4 secs

Fig.6-4: Exit standing mode IF Stroke reading > standing threshold OR Force gradient > 3/4 first step gradient

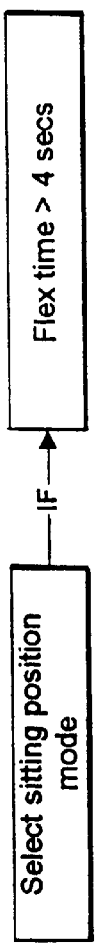

Fig.6-5: Select sitting position mode IF Flex time > 4 secs

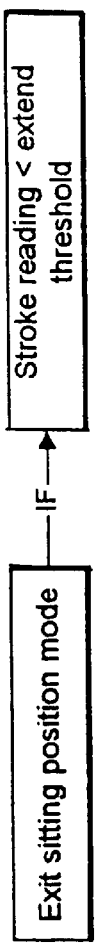

Fig.6-6: Exit sitting position mode IF Stroke reading < extend threshold

Fig.6-7: Select locked mode —IF→ Repeated load and unload at timed intervals —AND→ Limb extended during activation sequence Fig.6-8: Exit locked mode —IF→ User activated hardware device (eg switch)

Fig.6-9: Select stairs descent mode —IF→ Repeated load and unload at timed intervals —AND→ Limb extended during activation sequence Also: Max flat flex + stairs offset < flex period < 2 secs —AND→ Stroke reading > min peak swing level for flat walk Fig.6-10: Exit stairs descent mode —IF→ User activated hardware device (eg switch); Flex period < max flat flex Fig.6-11: Select Stumble Mode —IF→ Walking speed < max flat walking speed —AND→ Extend period < 3/4 minimum extend period for selected walking speed —OR→ Positive gradient detected after negative gradient during flexion Fig.6-12: Exit Stumble Mode —IF→ Stroke reading < extend threshold

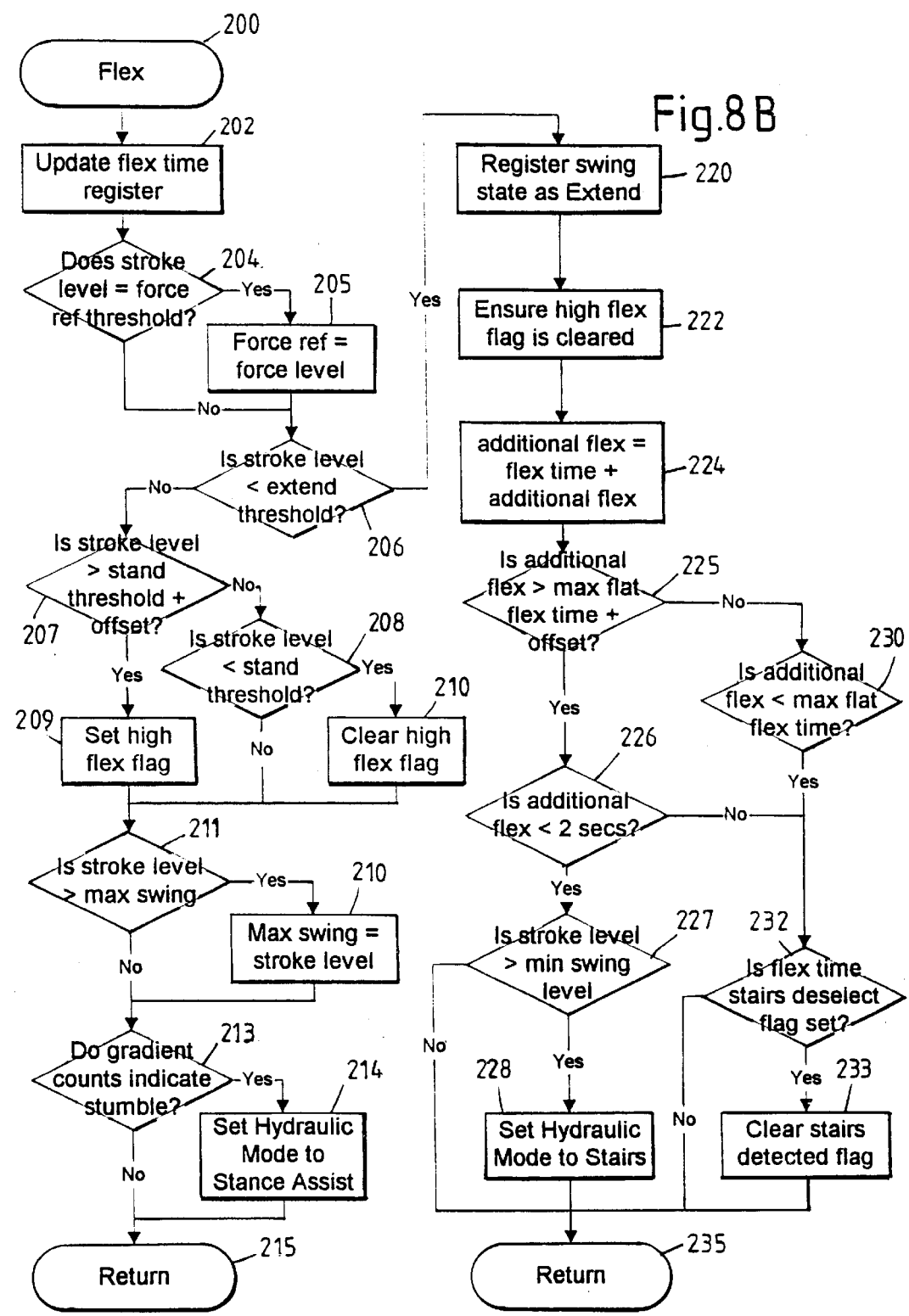

LOWER LIMB PROSTHESIS

This invention relates to a lower limb prosthesis incorporating an adaptive prosthesis control system in the form of a processor-controlled knee flexion control unit which is arranged to resist the flexion at the knee joint in a variable way according to signals picked up from a sensing means on the prosthesis and processed in accordance with a stored program.

British Patent Application No. GB 2216426A discloses such a lower limb prosthesis. A pneumatic cylinder assembly is used as the knee flexion control unit to provide resistance to knee flexion and extension during the swing phase of the walking cycle. This unit includes a valve which is adjustable using a stepper motor to alter the degree of resistance according to signals received from a processor which senses walking speed, so that resistance to movement of the shin component about the knee axis is varied as the walking speed varies.

British Patent Application No. GB 2280609A teaches the programming of an adaptive prosthesis control system using a remote operator control unit allowing convenient setting up of the system by a prosthetist using a handheld remote control unit, whereby walking tests can be conducted at different speeds and a complete set of control data in which flexion resistance settings are mapped onto walking speed ranges can be quickly programmed. In the prosthesis described in Application No. GB 2280609A knee stability is achieved during the stance phase by means of a mechanical load-activated knee braking device consisting of an expandable brake shoe with a friction lining, housed in a brake drum.

One of the difficulties associated with the above-mentioned mechanical friction brake for knee stabilisation during the stance phase is its comparatively sharp transition from a condition in which the knee is free to flex to one in which it is locked. An alternative stance control device found in other lower limb prostheses makes use of a hydraulic piston and cylinder assembly which provides yielding resistance to flexion during the stance phase. This allows the amputee in many cases to achieve a more natural gait due to the ability to roll over the foot in mid stance while achieving smooth initial flexion at the knee. Extension of the knee prior to heel contact is assisted by a coiled compression spring inside the cylinder. However, the need to compress the spring during the latter part of the preceding stance phase leads to many amputees finding such an hydraulic swing and stance control unit tiring to use. The unit also tends to be difficult to adjust in many cases and the mechanism for controlling the onset and release of stance control can produce an unnatural gait.

It is an object of the present invention to provide improved control of knee flexion for a wide variety of amputees and in a wide variety of circumstances.

According to one aspect of this invention, a lower limb prosthesis for an above-knee amputee has an adaptive control system which comprises a knee flexion control device arranged to resist flexion at the knee joint both hydraulically and pneumatically. Sensor means may be provided for generating electrical sensor signals in response to loading of the prosthesis, together with an electronic processing circuit electrically coupled to the sensor means and the control device for automatically adjusting the hydraulic and pneumatic resistance to knee flexion according to the actions of the amputee, the system being arranged such that the resistance to knee flexion is controlled at least predominantly hydraulically during the stance phase of the walking cycle of the prosthesis and at least predominantly pneumatically during the swing phase of the walking cycle. Preferably, the system is configured such that knee flexion is hydraulically resisted substantially only within an initial part of the angular range of flexion of the knee from full extension, typically from zero to between 30° and 35° flexion. Conveniently, extension assistance can be provided pneumatically by the same control element which resists flexion during the swing phase, and terminal extension damping may be achieved hydraulically.

This advantageous combination may be provided in the form of a posteriorly mounted piston and cylinder assembly having two pistons mounted coaxially on a common piston rod and reciprocable together within respective chambers, one containing hydraulic fluid and the other containing a gas, e.g. air. In each case the flow of liquid or gas to or from the respective chambers may be restricted by valves automatically controlled in response to setting signals from the processing circuit whereby the resistance to flexion provided by the hydraulic part of the assembly is varied according to the mode of ambulation of the amputee (such as level walking, walking up or down an incline, walking up or down stairs, and so on), while resistance of the pneumatic part of the assembly is controlled according to the sensed speed of walking, as described in the above-mentioned prior published patent specifications. Arranging for the hydraulic part of the piston and cylinder assembly to resist flexion only during the first 30° to 35° of flexion limits the effect of the hydraulic part mainly to resisting flexion during the stance phase and, with appropriate directing of the hydraulic fluid, damping forward movement of the prosthesis shin part towards the end of the swing phase so as to cushion extension of the knee joint prior to terminal impact at the end of the swing phase.

Adjustment of a pneumatic piston and cylinder assembly according to walking speed by means of a needle valve driven by a stepper motor is described in detail in GB 2280609A. Compression of air against the needle valve during swing phase flexion, together with the comparatively small resistance provided by the hydraulic part of the assembly at large angles of flexion brings the advantage of efficiently generated extension assistance due to the compressed air cushion which exists at maximum flexion, obviating the need for a stiff extension assisting spring, as in prior hydraulic units. The preferred technique for controlling resistance to knee flexion during the stance phase using a piston in a chamber containing incompressible hydraulic fluid makes use of a variable orifice in a first bypass passage between ports in opposite end portions of the chamber and on opposite sides of the piston, the orifice area being controlled electromechanically using, for example, a stepper motor to move a valve member to different positions according to detected modes of amputee activity.

Provision of hydraulic and pneumatic resistance to flexion, both programmable according to activity mode, allows a wide range of adjustment which can be achieved precisely. For instance, coarse adjustment can be performed hydraulically and fine adjustment pneumatically. In this way, it is possible for the prosthetist to program the system to match the level of stance control to the residual muscular control available from the amputee.

The applicants have found that a particular improvement of the ease with which an above-knee amputee can descend a ramp can generally be obtained by increasing stance phase flexion resistance in comparison with the optimum setting for level walking. Consequently, in the preferred control system in accordance with this invention the sensor means and the processing circuit are operable together to generate a descent control signal indicative of the amputee walking down a slope or ramp, this descent control signal causing the stepper motor to move the valve member in the hydraulic bypass passage so as to restrict fluid flow to a greater degree than when the amputee is walking on the level.

Sensing of the ramp descent mode is advantageously performed by means of the processing circuit in combination with a sensor located at the knee level to provide a sensor output signal indicative of kinetic and kinematic parameters around the knee such as knee bending moment, i.e. the moment tending to cause knee flexion during the stance phase. In particular, the processing circuit is arranged to detect an increase in the bending moment around the prosthetic knee with reference to a stored reference level, the increase being sustained over a period of time which occupies at least the major part of the stance phase, thereby to produce the descent control signal. The applicants have found that the above bending moment during the stance phase when the amputee is descending the ramp, while not necessarily reaching a higher maximum value than during level walking, generally remains high over an extended period of time, to the extent that the descending ramp mode can be sensed by monitoring the integral of the bending moment with respect to time. Accordingly, when the value of this integral exceeds a reference level, the descent control signal is generated. In order to distinguish the ramp descent mode from the level walking mode at different speeds of walking, the integral is normalised with respect to the stance phase duration or the total step cycle period. In general, then, the force at the knee level is sensed over a period of time covering at least the major part of the stance phase, the resulting signals being used to determine a predetermined signal pattern.

Sensing of a bending moment related to loading of the limb may be performed by means of a force sensing resistor mounted between, for example, relatively movable parts in the region of the knee joint, and a particularly preferred arrangement is to place the force sensing resistor between, on the one hand, one end of a lever arm the other end of which is pivoted on a knee chassis member forming part of the thigh part of the prosthesis, and, on the other hand, a resilient element inserted between the lever arm and the knee chassis to provide small amounts of flexion independently of the knee flexion control device. Other transducers may be used for producing an electrical signal which is wholly or partly a function of the knee bending moment. For instance, a friction-operated force sensing resistor may be provided around the knee centre, or it may be mounted inside one of the chambers of the piston and cylinder assembly. Alternatively, a strain gauge may be fixed on the lever arm referred to above or on the piston rod connecting the piston and cylinder assembly to the thigh part or shin part of the prosthesis, or a strain gauge may be fixed to the cylinder body itself or on the upper part of the shin member, i.e. above the connection of the piston and cylinder assembly to the shin part. Yet a further alternative is the fitment of a pressure sensing cell inside the hydraulic fluid-containing chamber or as a load bearing member forming part of one of the pivotal joints between the piston and cylinder assembly and the thigh and the shin parts of the prosthesis.

A second sensor is preferably used for sensing the step period. Particular advantages are obtained by using a proximity sensor, e.g. a magnetoresistive transducer in combination with a permanent magnet mounted respectively on parts which move relative to each other when the knee is flexed. Thus, a magnetoresistor may be mounted on the body of the cylinder of the piston and cylinder assembly, while a permanent magnet is mounted on the piston rod or one of the pistons so that the distance between the magnet and the transducer varies from a minimum value to a maximum value when the knee is flexed between full extension and full flexion or vice versa. The proportional nature of the output of a magnetoresistive sensor lends itself to stroke position sensing, which maps directly onto flexion angle, albeit non-linearly, allowing not only the measurement of step period, but also the instantaneous stroke position or flexion angle value, as well as swing phase and stance phase durations.

In accordance with the invention, other activity modes can be detected. In all modes, but at least the cases of walking and descending an incline, the control system allows the prosthetist to set the hydraulic resistance to knee movement to suit the detected mode and to suit the ability of the amputee in each mode. Different aspects of the invention include detection of stairs descent using detection of a knee flexed period during the swing phase which is higher than that normally obtained during walking together with a peak flexion angle which exceeds a predetermined threshold. According to another aspect, a stumble condition can be detected in response to an abnormally short knee extended period, an abnormally increasing flexion angle during the stance phase, or an increasing flexion angle following a decreasing flexion angle whilst the knee is in a flexed state. According to a further aspect of the invention, a standing mode and a sitting mode can be detected respectively in response to the knee extended state or the knee flexed state being longer than a respective predetermined period.

According to another aspect of the invention, the electronic processing circuit is arranged such that automatic adjustment of the resistance to flexion in response to changes in the actions of the amputee are brought about by feeding a descent control signal to the control device in response to detection of the amputee descending an incline such that the descent control signal causes an increase in the resistance of the control device to knee flexion compared with the resistance set for level walking.

According to yet a further aspect of the invention the electronic processing circuit is. arranged automatically to adjust the resistance to knee flexion in response to changes in the sensor signals occurring when the amputee moves from walking on a level surface to walking down an incline and vice versa. In addition, adjustment of the hydraulic resistance to flexion may occur in response to changes in the sensor signals occurring when the amputee sits down, stands up, stops walking, and starts walking, by monitoring both the load on the prosthesis and the flexion angle with respect to a predetermined time period in the order of 2 to 7 seconds.

In the preferred knee flexion control device, independent hydraulic flexion and extension resistance is provided using dual bypass passages effective at low flexion angles, one passage containing a motorised valve for dynamic alteration of flexion resistance during the stance phase, and the other containing an adjustable valve which maybe manually operated for adjusting the stiffness of terminal extension damping at the end of the swing phase. In effect, the latter valve overrides the motorised valve on the extension stroke by appropriate direction of hydraulic fluid through the bypass passages using non-return valves.

A preferred embodiment of the invention will be described below with reference to the drawings. By combining both hydraulic and pneumatic control of knee movements in a single, compact control unit, with the movement in both the hydraulic and pneumatic parts of the unit regulated by microprocessor controlled electromagnetic actuators such as electric motors, a particularly versatile and effective control system is provided, allowing an amputee to achieve good gait characteristics not only during level walking at various speeds, but also on inclines. These benefits are obtained substantially without unnatural movements of the limb to trigger operation of the control system, and the prosthesis also offers advantages for standing, sitting, and negotiating stairs. The hydraulic flexion resistance, which provides knee stability during the stance phase, complements the amputee's voluntary muscular knee stabilisation to a degree which is variable according to the amputee's strength, dynamic variation being possible so that the level of stabilising assistance can be varied according to the mode of activity.

BRIEF DESCRIPTION OF THE DRAWINGS

FIGS. 6-1 to 6-12 are diagrammatic representations of activity mode detection criteria;

FIG. 7 is a flowchart of mode detection occurring during a playback portion of the program;

FIGS. 8A and 8B together constitute a flow chart illustrating mode detection in more detail during ambulation;

FIG. 9 is a mode-responsive valve setting routine flow chart; and

FIG. 10 is a speed-responsive valve setting routine flow chart.

DETAILED DESCRIPTION OF THE INVENTION

Figure 1:
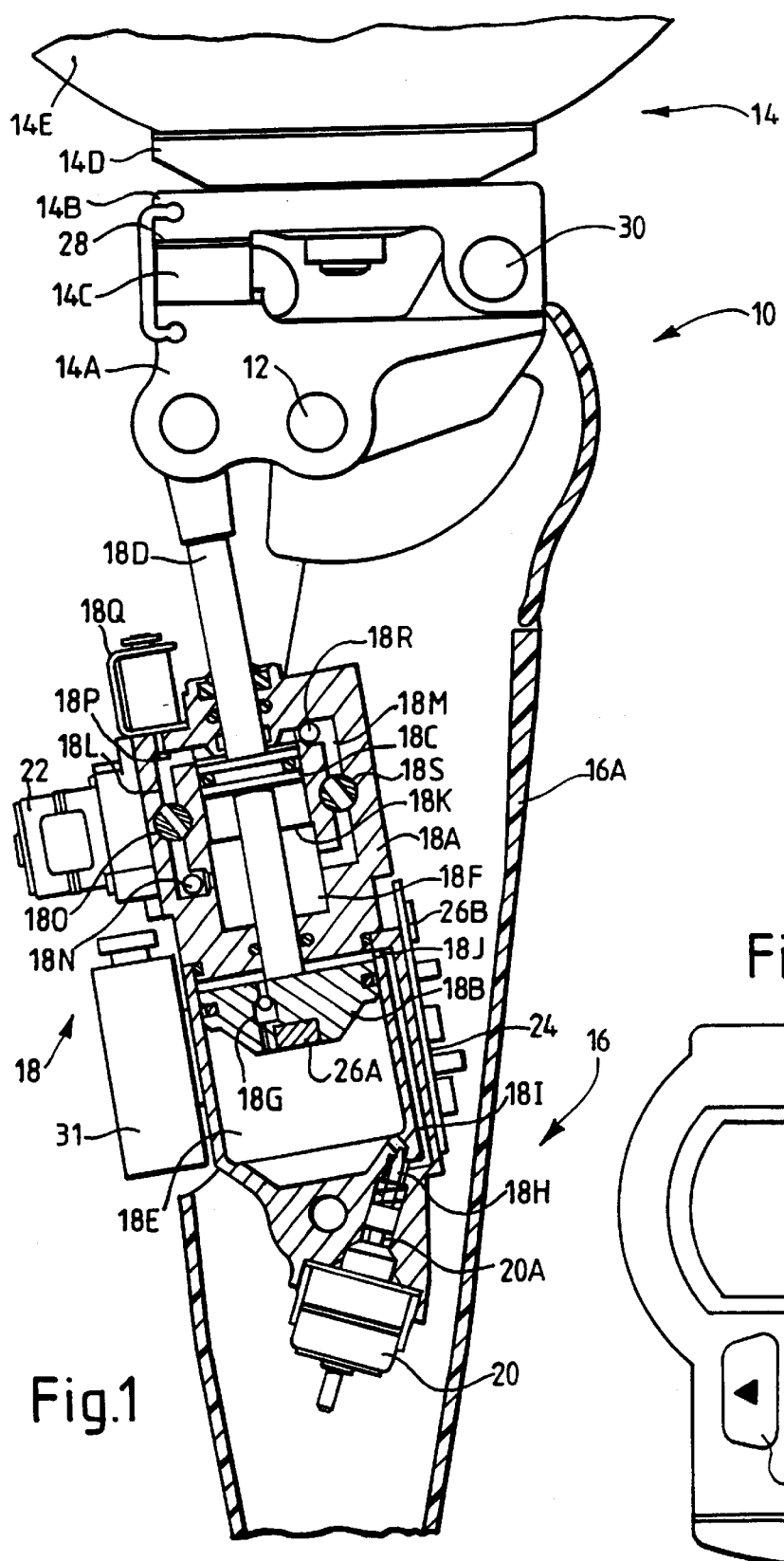
FIG. 1 is a partly sectioned side elevation of part of a lower limb prosthesis including a knee flexion control unit and electronic control elements which form part of an adaptive control system.

Part of a lower limb prosthesis in accordance with the invention, incorporating an adaptive control system, is shown in FIG. 1. The prosthesis has a knee joint 10 with a knee pivot 12 defining a knee axis and connecting a thigh component 14 to a shin component 16. The thigh component comprises a knee chassis 14A, and an anteriorly pivoted mounting plate 14B arranged to compress a posteriorly mounted elastomeric spring element 14C against the knee chassis when the prosthesis is loaded. The thigh component also has an alignment device 14D and a stump socket 14E. The shin component 16 has a fibre-reinforced composite shin cradle 16A which houses a piston and cylinder assembly 18 acting as a flexion control device. The assembly 18 comprises a cylinder 18A which is pivotally coupled to the posterior part of the shin cradle 16A and two coaxial, longitudinally separated pistons 18B, 18C having a piston rod 18D which is pivotally coupled to the knee chassis 14A.

The piston and cylinder assembly 18 is a hybrid pneumatic and hydraulic device with the first piston 18B, hereinafter referred to as the "pneumatic piston", reciprocable in a first, pneumatic piston chamber 18E and the second piston 18C, hereinafter referred to as the "hydraulic piston", reciprocable in a second, hydraulic chamber 18F. The arrangement and function of the pneumatic piston 18B and associated parts of the flexion control device are generally similar to those of the piston and cylinder assembly disclosed in the above-mentioned prior patent specification GB 2280609A. It will be noted that the pneumatic piston 18B contains a bypass passage 18G including a non-return valve which is oriented such that the pneumatic piston 18B resists movement of the piston rod 18D much more during flexion of the knee joint than during extension. Indeed, resistance to extension is almost negligible. Resistance of the pneumatic part of the assembly 18 to flexion at the knee joint is controlled by a needle valve 18H which is adjustable by a first electrical stepper motor 20 and an associated screwthreaded shaft 20A connected to the needle member of the needle valve. The needle valve 18H lies in a passage 18I in the body of the cylinder 18A, the passage interconnecting the upper and lower parts of the chamber 18E on opposite respective sides of the pneumatic piston 18B, and emerging at a port 18J in the wall of the cylinder. Operation of the motor 20 causes the shaft 20A to move axially so that the needle member moves into or out of a passageway forming part of passage 18I to vary the orifice area.

The passage 18I constitutes a second bypass passage interconnecting the chamber spaces on opposite sides of the pneumatic piston 18B. It will be understood, then, that the flexion resistance provided by piston 18B depends largely on the setting of the needle valve 18H by the motor 20.

Turning attention now to the hydraulic part of the piston and cylinder assembly 18, it will be noted from FIG. 1 that the chamber 18F housing the hydraulic piston 18C has two regions of differing diameter. That part of the chamber 18F which contains the hydraulic piston 18C at full extension of the knee joint and at small angles of flexion has a diameter such that the piston 18C tightly seals against the walls of the chamber. Beyond an intermediate transition feature 18K the cross-section of the chamber 18F is such that the piston 18C, at larger angles of flexion, is no longer a sealing fit against the walls of the chamber. This means that the orifice areas of bypass passages 18L and 18M, which are formed in the body of cylinder 18A so as to connect parts of the chamber 18F on opposite sides of the piston 18C, control the movement of hydraulic fluid from one end of the chamber to the other only during an initial flexion angle range, in this case from 0° to 30° flexion at the knee axis. As a result, and since an hydraulic piston and cylinder arrangement is able to (and in this case is arranged to) generate much higher resisting forces than a pneumatic piston and cylinder arrangement of comparable size, the resistance to flexion and extension during the first 30° of knee flexion is controlled predominantly by the hydraulic part of the control device 18, while the resistance to flexion at larger angles of flexion is controlled predominantly by the pneumatic part of the unit 18. Furthermore, since flexion during the stance phase of the walking cycle invariably remains within the 0° to 30° range, whereas flexion during the swing phase generally exceeds 30° by a considerable margin, this hybrid hydraulic and pneumatic unit provides predominantly hydraulic control of flexion and extension during the stance phase and predominantly pneumatic control of flexion and extension during the swing phase.

The first hydraulic bypass passage 18L contains a non-return valve 18N oriented so as to close the passage during knee extension movements. The passage 18L also contains an adjustable rotary valve 18O connected via a gear mechanism (not shown) to a second stepper motor 22 mounted on the side of the wall of cylinder 18. Variable valve 18O has a through passage which communicates with the bore of passage 18L to a varying degree depending on the angular position of the valve member containing the groove, the cross-section of the passage being shaped to provide a progressive change in orifice area as the rotatable part of the valve is driven by the motor 22. Due to the orientation of the non-return valve 18N, the first hydraulic bypass passage 18L and its associated valve 18O control the level of knee flexion resistance due to the hydraulic part of the assembly 18 according to the electrical signals controlling the second stepper motor 22.

In this preferred control unit, a secondary flow-restricting element is provided in passage 18L, in the form of a plug 18P operated by a solenoid 18Q. This has uses when a high level of flexion resistance is required more rapidly than can be achieved with stepper motor 22. The second bypass passage 18M in the hydraulic part of assembly 18 has a non-return valve 18R which is oppositely oriented to that of passage 18L such that the second rotary valve 18S, which restricts the flow of hydraulic fluid through passage 18M controls the resistance to knee extension at angles of flexion less than 30°. This second rotary valve 18S is, in this case, manually presettable, and determines the terminal impact cushioning just prior to heel contact at the end of the swing phase.

The two stepper motors 20, 22 are driven by the combination of a microcomputer and receiver which together form electronic assembly 24 in the form of a printed circuit board which, in this embodiment, is secured to the outside of the cylinder 18A, as shown in FIG. 1. The microcomputer receives sensor signals from two sensor devices. The first is a magnetic proximity sensor comprising the combination of a permanent magnet 26A housed in the piston assembly constituted by pistons 18B, 18C, and 18D (here it is recessed within piston 18B), and a magnetoresistive transducer 26B which is so mounted on the outside of cylinder 18A that the change in distance between magnet 26A and transducer 26B is unidirectional as the piston rod 18B moves from one limit of its stroke to the other. Since the sensor constituted by the combination of magnet 26A and the magnetoresistive transducer 26B is a proximity sensor, the output of the magnetoresistive transducer is representative of the position of the piston assembly in its stroke within cylinder 18A and, hence, is representative also of the instantaneous flexion angle of the knee.

The other sensor coupled to the microcomputer is a force sensing resistor 28 which is sandwiched between the load-sensitive combination of the mounting plate 14B and the knee chassis 14A. The mounting plate 14B acts as a lever arm pivoted about its anterior pivot 30 which is anteriorly spaced from the knee axis represented by knee pivot 12. Since the force sensing resistor 28 is acted upon at a distance from pivot 30 and is at the knee level of the prosthesis, the force it experiences is mainly a function of the bending moment applied to the knee through socket 14E, this being due partly due to the weight of the amputee and the muscular effort applied at the hip.

In summary, then, the microcomputer receives two sensing signals representative of the activity of the amputee, one which is a function of piston stroke or knee flexion angle, and the other which is a function of the knee bending moment in the anterior-posterior plane.

The electronic circuitry 24 and the two stepper motors 20, 22 are powered by a battery which is indicated by reference 31 in FIG. 1. The receiver has a receiving antenna formed as a conductor track on the printed circuit board bearing components of the microcomputer and receiver.

Figure 2:
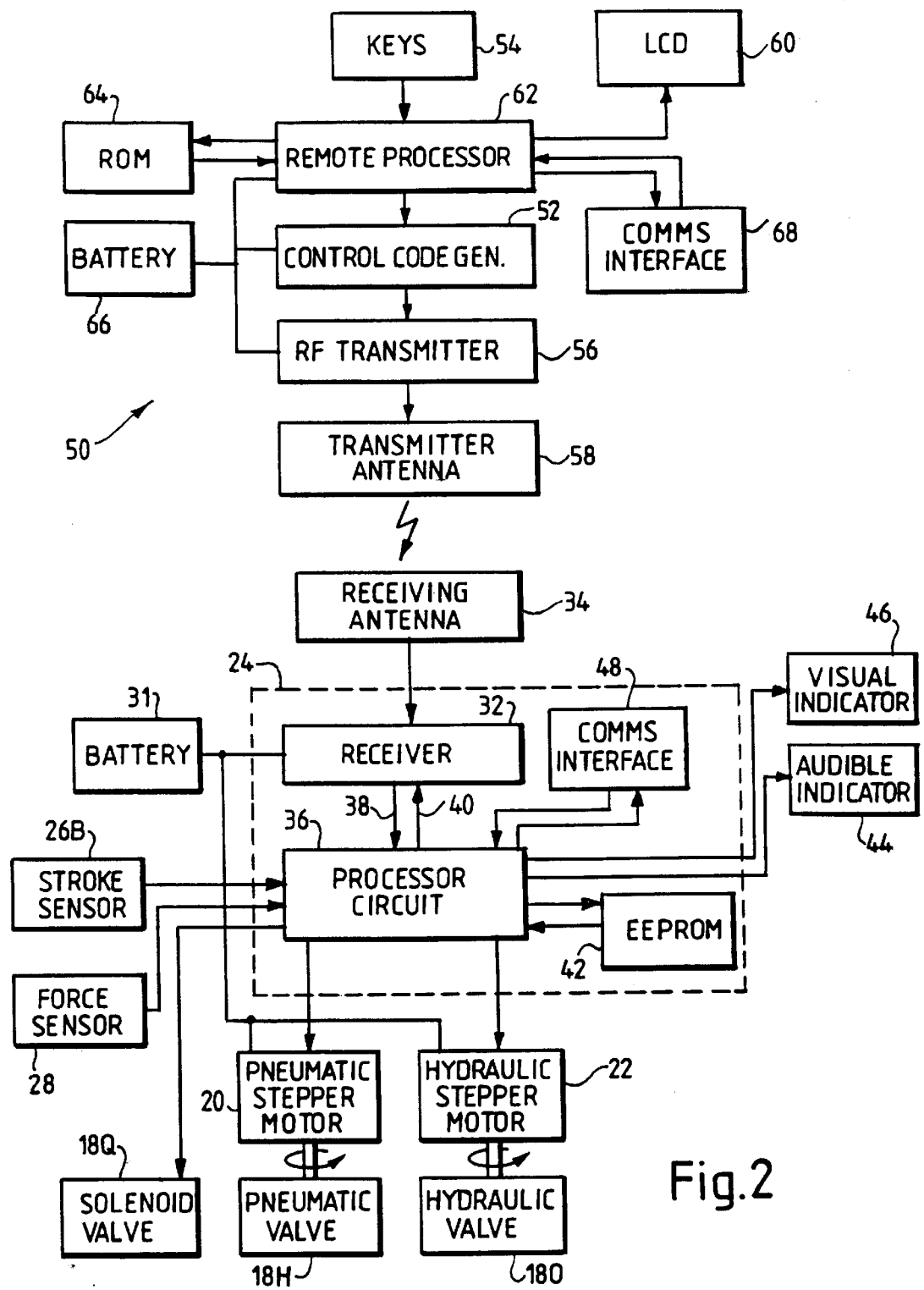
FIG. 2 is a block diagram of the adaptive control system.

The electronic circuitry 24 and the sensors are shown in more detail in FIG. 2. More particularly, the circuitry comprises the receiver 32 coupled to an antenna 34 and a processor circuit 36 which receives demodulated signals via input 38 and controls the powering of the receiver via output 40. A non-volatile memory in the form of an EEPROM 42 stores walking speed and valve setting data produced by the processor circuit 36, and writes such data to the processor circuit 36 when required.

The processor circuit 36 includes output drivers for driving the stepper motor 20 (for pneumatic control) and the stepper motor 22 (for hydraulic control) which, respectively, operate needle valve 18H and rotary valve 18O. Input ports to the processor circuit 36 receive inputs not only from the receiver, but also from the force sensing resistor 28 and magnetoresistive transducer 26B (see FIG. 1). Further outputs from the processor circuit 36 are provided for driving the solenoid 18Q (see FIG. 1), as well as audible and visual indicators 44, 46 for providing status indications to the amputee or prosthetist (particularly for indicating when the receiver is switched on and/or when certain functions are selected using the operator control unit 50). A serial communications interface allows, for example, diagnostic signals to be sent to and received from the processor circuit 36. The receiver 32 preferably receives radio frequency (RF) signals via the receiving antenna 34 from an operator control unit 50 shown in block diagram form in FIG. 2 and in plan view in FIG. 3. The control unit 50 has a control code generator 52 responsive to operation of keys 54 on the face of the unit 50. The control codes generated by the generator 52 are modulated and transmitted by an RF transmitter 56 which feeds RF output signals to a transmitting antenna 58 within the control unit 50 for transmission to the receiving antenna 34 on the prosthesis. A display 60, here a liquid crystal display (LCD), together with a processor 62 and a pre-programmed read-only memory (ROM) 64 allow the operator control unit 50 to be menu-driven in the sense that keys 54 perform several different functions depending on the menu selections effected. ROM 64, being an external memory device, can be interchanged in order to vary the functions provided by the control unit 50. Details of the menu sequencing of the operator control unit 50 are not described here since they follow conventional patterns. Thus, using only three keys 54, a variety of functions can be performed, such as Increase, Decrease for setting speed, and pneumatic and hydraulic valve openings, and Select for selecting different parts of a teach routine, and for saving adjustments, all according to prompts in the display 60.

The operator control unit 50 is powered by a battery 66 housed within the unit casing (see FIG. 2), and a second serial communications interface 68 is provided for, for example, diagnostic purposes.

Figure 4:
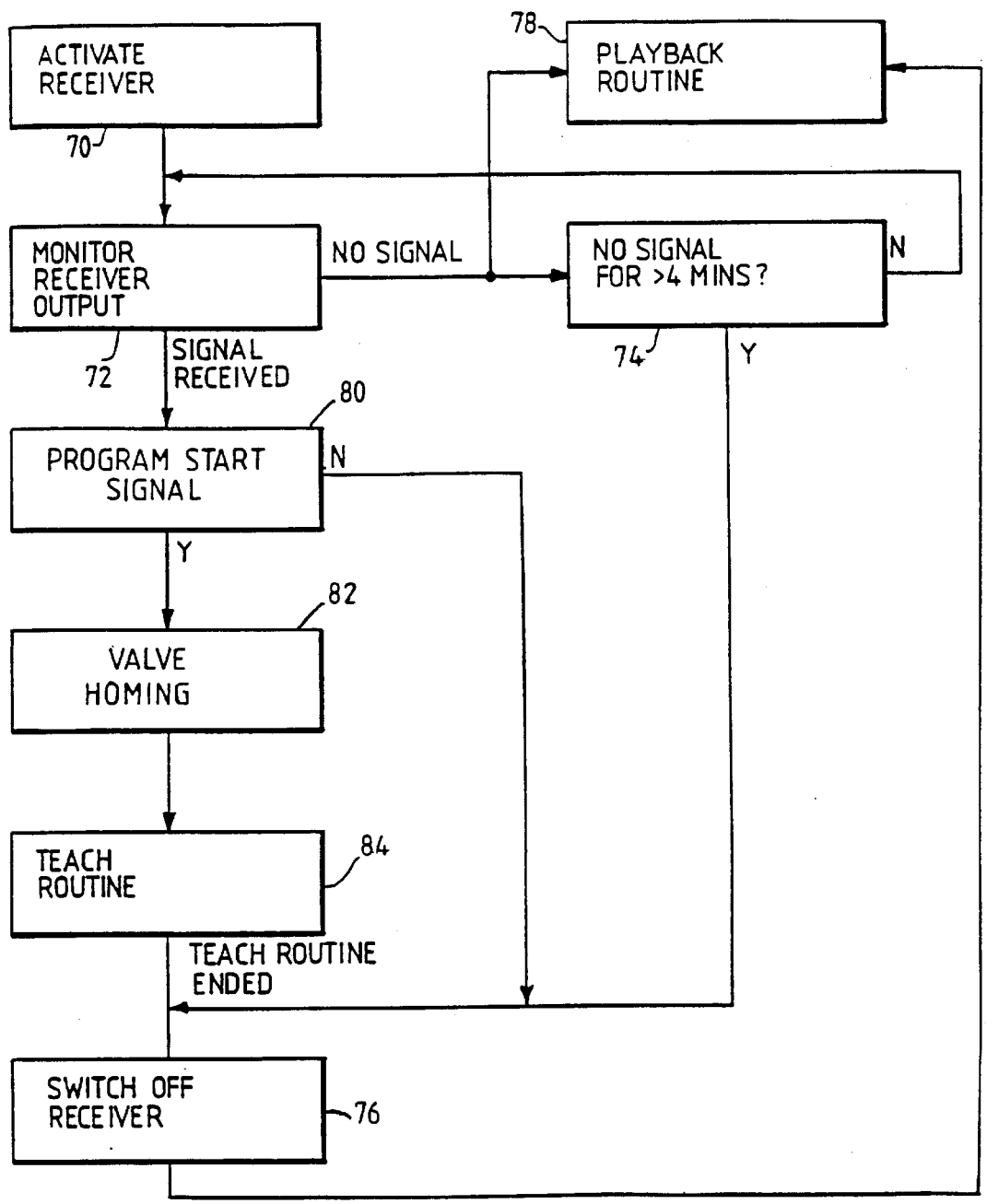
FIG. 4 is a flow chart illustrating start-up and shut-down phases of a program forming part of the control system.

Operation of the adaptive control system will now be described with reference to FIGS. 4 to 8. Referring firstly to FIG. 4, which shows start-up and shutdown phases of a program run by the microcomputer to cause the system to run in a teach mode, activation of the receiver 32, which remains off during a playback mode of the system to save battery power, is performed by flexing the prosthesis at the knee in a particular manner. Specifically, the patient flexes the limb fully, counts 10 seconds, then extends the limb within 10 seconds, and flexes it again. This produces a particular sequence of signals from the stroke sensor shown as 26A, 26B in FIG. 1 which are recognised by the processor circuit 36 as an activation code, and the receiver 32 is switched on via line 40 (FIG. 2) (step 70 in FIG. 4). Having activated the receiver 32, the software causes the processor circuit 36 to monitor the receiver output (step 72) for a signal from the operator control unit. In the absence of any signal for longer than a predetermined period (e.g. 4 minutes), the processor circuit 36 causes the receiver to be switched off again (steps 74 and 76). Absence of the signal from the operator control unit also causes the processor to operate the playback routine (step 78), which will be described below.

As soon as the signal from the operator control unit is detected, the processor circuit 36 waits for a program START signal from the operator control unit (step 80). If this is received, the microprocessor circuit operates a valve homing step (step 82) followed by a teach routine 84 which will be described below. If the START signal is not received, the receiver is switched off. The end of the teach routine 84 also produces switching off of the receiver as represented by step 76. The valve homing procedure (step 82) allows the stepper motors 20, 22 (FIG. 1) and valves of the pneumatic and hydraulic knee flexion control devices to be set with respect to a predetermined reference position defined by their limits of travel.

When the processor circuit 36 is operating in the teach mode, it continuously monitors movements of the prosthesis in order to determine whether the amputee is sitting, standing, walking, running, descending a slope and so on. If the patient is walking or running, the speed of such walking or running is determined. Thus, the stroke sensor is monitored insofar as pulses from the transducer 26B are received in the microprocessor circuit 36. The spacing between the pulses is measured by a counter loop (only two successive pulses are required to establish a measurement), and a running average of the step period is calculated. If the step period represented by the running average is greater than two seconds, a speed register set up by the processor circuit is reset and the next step period is counted. If no movement is detected for a predetermined period such as 4 seconds, the circuit 36 is programmed to cause the stepper motors 20, 22 to drive the respective valves to settings stored in the EEPROM for standing or sitting.

Averaging of the speed may be performed by creating a predetermined number, e.g. six, of calculation registers and successively feeding them a corresponding number (six) of step period counts, each register commencing with a different step. Thus, a first calculation register receives the counts for, say, steps 1, 2, 3, 4, 5, and 6. The second calculation register stores the counts for steps 2, 3, 4, 5, 6, and 7, the third register receives the counts for steps 3, 4, 5, 6, 7, and 8, and so on, the contents of each register being added and divided to produce a respective average value so as to yield a running average by reading the successive calculated averages one after the other at the same rate as the registers are being filled. In practice, the average is calculated by counting how many steps are taken between resets of the registers, ignoring the first and second step periods, adding together the next four and dividing by four. Other methods of calculating a running average can be used. The running average is stored in a walking speed register which is being continuously updated with the new average values. In the teach mode, updating continues only so long as the values are representative of the patient walking.

It will be appreciated that, having determined the walking speed in the above described manner, and given stored data in the form of a look-up table of valve settings associated with particular walking speeds, it is possible during use of the prosthesis to set the pneumatic valve 18H (FIG. 1) dynamically so as to vary the resistance to flexion during the swing phase. Similarly, such stored datacan contain a table of hydraulic valve settings for dynamic variation of the hydraulic valve 18O (and, if required, the pneumatic valve 18H) according to a sensed activity mode of the amputee (e.g. walking, descending a slope, sitting, standing and descending stairs). The manner in which this stored data is produced will now be described with reference to FIGS. 5A and 5B, showing the teach routine performed by the processor circuit 36.

The teach routine contains the basic operations of a prosthetist using the operator control unit to select activity modes of the patient such as sitting, standing, walking, running, descending a slope, descending stairs, etc. A series of tests may be carried out in each of these modes while the pneumatic and hydraulic valves are adjusted as appropriate. To take an example, for the walking mode, the prosthetist can use the operator control unit to designate certain walking speeds as "slow", "normal", or "fast", the amputee being led through a series of walking tests at the different speeds while the valves are adjusted by remote control until a satisfactory gait is obtained in each case. The optimum valve settings so obtained are stored by "saving" corresponding signals, with the processor in the prosthesis then if necessary, performing calculations to derive intermediate values so that data is stored in "final" registers set up by the processor circuit 36, as described in the above-mentioned prior Application No. GB 2280609A. When the receiver is switched off (step 76. FIG. 4) the saved data is read into the EFPROM (42 in FIG. 2).

Figure 5A:
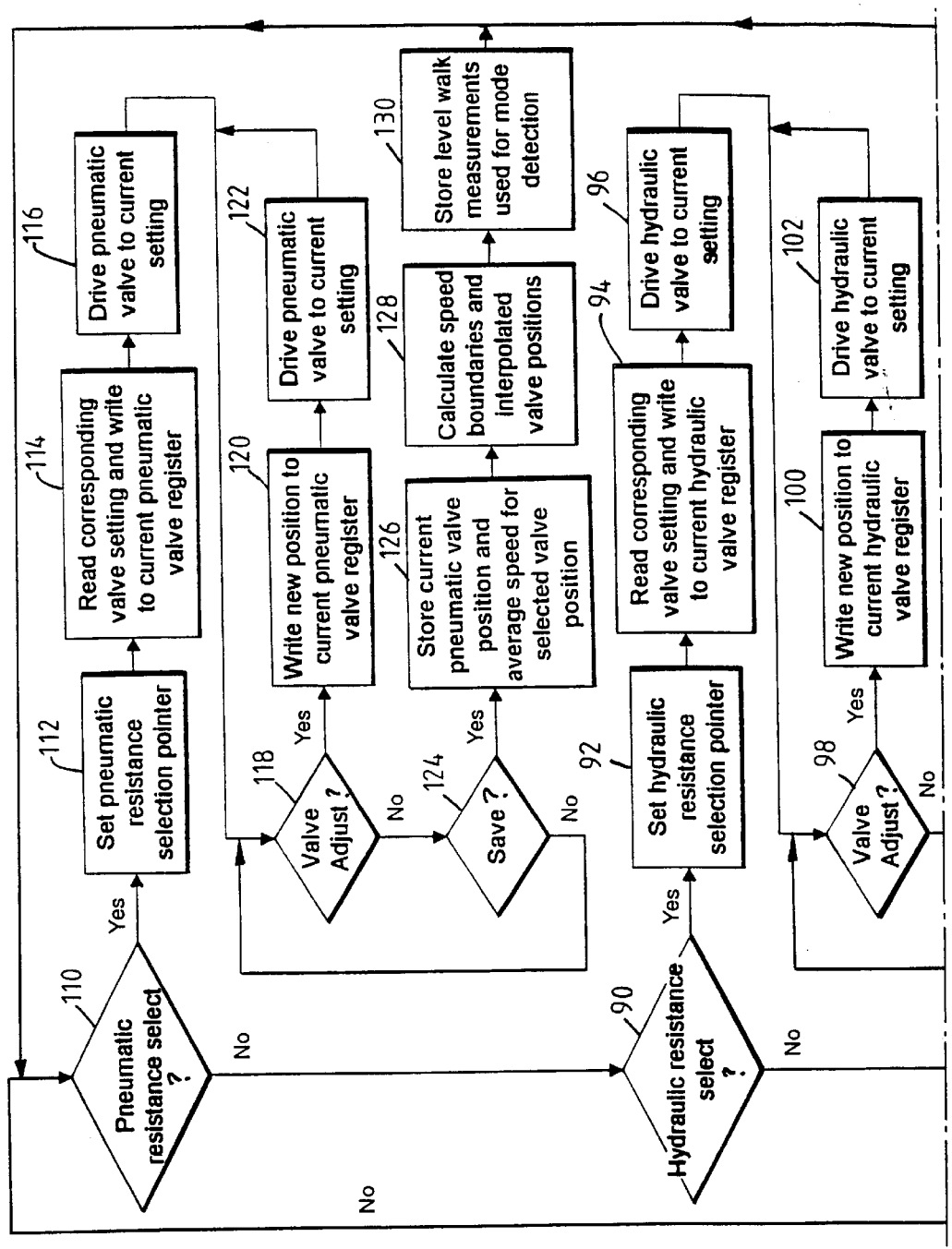
FIGS. 5A and 5B together constitute a flow chart of a teach routine of the program.
Figure 5B:
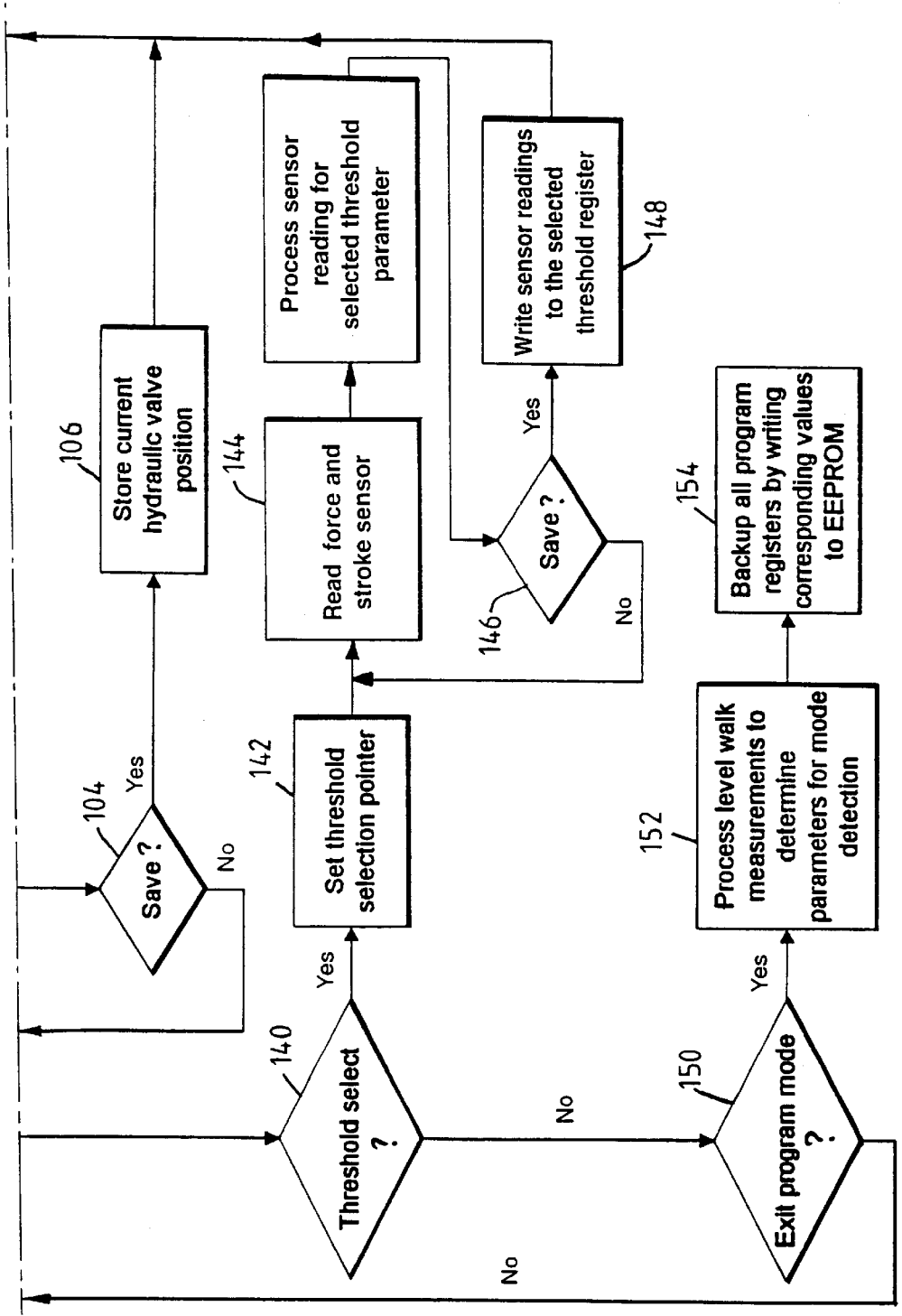

Now referring to FIGS. 5A and 5B, a SELECT (S) button on the operator unit (see FIG. 3) is used by the prosthetist to select first of all an hydraulic resistance select routine (selection step 90). The display 60 on the operator control unit prompts the prosthetist to select the activity mode which, at this stage, would usually be "level walking" which sets an hydraulic resistance selection pointer in the program (step 92 ) and the currently stored setting of the hydraulic valve 18O for "level walking" is read from the store and written to an hydraulic valve register (step 94) for driving the valve 18O to that current setting (step 96). Next, the operator is presented with the prompt "Valve Adjust" (step 98), which allows adjustment of the hydraulic valve 18O for changing the yield of the piston and cylinder assembly during the stance phase for level walking. Thus, the control unit buttons 54 (FIG. 3), may be used to increase or decrease the hydraulic resistance to flexion (see steps 100 and 102 in FIG. 5A). Once the prosthetist is satisfied with the yield setting, the operator control unit buttons are pressed to save the valve setting whereupon it is stored in the "final register" (steps 104, 106). Generally, this hydraulic valve setting operation is performed only approximately at first, with or without a walking test, more precise adjustment being performed later in a full walking test.

Having achieved an approximate yield setting, and when the amputee has taken a few steps to become used to the yield, the pneumatic resistance select operation is selected (step 110 in FIG. 5A), whereupon the operator is prompted to enter a walking speed. Usually, at this stage, the speed designation will be "normal" (i.e. a medium walking speed) whereupon the pneumatic resistance selection pointer for the needle valve 18H (see FIG. 1) is set to "normal" (step 112) and the valve is driven to the current setting which is read from the control data and written into the current pneumatic valve register (steps 114, 116). Having now selected a "normal" walking speed, the operator can, if necessary, adjust the pneumatic valve to obtain at least a satisfactory gait at the normal walking speed using valve adjustment and setting steps 118, 120, and 122, the processor circuit driving the valve 18H via stepper motor 20 to the required setting (see FIGS. 1 and 2). Saving the adjusted valve setting (step 124) causes the processor circuit 36 (FIG. 2) to store the new valve setting together with the associated speed of walking measured during the walking test in which the valve setting was obtained (step 126) and then to calculate a new set of control data for the pneumatic valve based on the new "normal speed" valve setting together with previously derived valve settings for associated "slow" and "fast" measure walking speeds, the control data taking the form of a series of walking speed ranges delimited by speed boundaries, and interpolated valve positions. The manner in which such control data is calculated is described in more detail in the above-mentioned prior Application No. GB 2280609A. These steps are shown in FIG. 5A as steps 126 and 128. At the same time, other measurements automatically obtained during the walking test, such as the stance duration and the bending moment profile (as measured by the magnetoresistive sensor 26B and the force sensing resistor 28 (see FIG. 1) respectively) are stored for use in mode detection in the playback routine which is described hereinafter (step 130). Indeed, in this preferred embodiment of the invention, the force sensing resistor measurements are used in conjunction with the stance duration measurement to derive a "ramp mode detection index" which will be described in more detail below.

The adaptive control system now contains at least approximate settings of the hydraulic and pneumatic valves for the normal walking speed, and hence for flexion resistance during stance and swing phases respectively. Generally, it will now be necessary to adjust the stance phase yield (i.e. the hydraulic valve) more precisely, which the operator does by selecting once again the hydraulic resistance adjustment routine shown in FIGS. 5A and 5B as steps 90, 92, 94, etc. to step 106. Steps 98, 100, and 102 are repeated while the patient is walking until the optimum yield setting is achieved.

As described above, the hydraulic part of the control unit 18 includes a terminal impact cushioning facility. At this stage, valve 18S (FIG. 1) is manually adjusted if necessary to alter the degree of cushioning, and the stance phase yield can be checked again, if necessary.

The teach routine also includes the facility to select threshold levels of the sensor output signals from the magnetoresistive transducer 22B and the force sensing resistor 28 (FIG. 1) for use in detecting certain amputee activity modes. This facility appears as steps 140 142, 144, 145, 146 and 148 in FIG. 5B. A particular example of threshold selection which the operator may perform is to establish the force sensing resistor output magnitude and the stroke magnitude and/or period for distinguishing between walking, standing and sitting, bearing in mind that when standing some movement at the knee normally occurs. Other thresholds which can be set using this facility are the flex and extend thresholds, defining the magnetoresistive transducer output levels at the transition from the stance phase to the swing phase and from the swing phase to the stance phase respectively. This enables the processing circuit to time the duration of the stance and swing phases.

So far, in the exemplary test procedure set out above, valve settings for walking at normal speed only have been obtained. Usually, it is not necessary to alter the stance phase flexion resistance (the yield) at different walking speeds. However, the swing phase resistance as determined by the pneumatic valve setting alters according to walking speed, and the prosthetist can now perform the pneumatic resistance selection steps 110, 112, 114 to 130 whilst the patient walks at a slow walking speed and then at a fast walking speed respectively. Again, a new set of control data with new speed boundaries and interpolated valve positions is obtained.

One of the main benefits of being able to alter yield during the stance phase is the ability to provide different optimum settings for level walking and walking down a slope. For the latter function, the prosthetist may now perform a ramp descent test whereby the amputee is asked to walk down a ramp of a predetermined incline at a normal speed while the hydraulic valve is adjusted until an optimum setting is obtained. This is achieved using steps 90, 92, 94, etc. to 106 in FIGS. 5A and 5B, the initial hydraulic resistance selection pointer being set to the "ramp descent" mode in step 92. Similarly these steps may be used for setting an optimum hydraulic valve setting for standing and other activity modes.

In summary, then, the teach routine involves successive tests in which the hydraulic part of the control unit is adjusted to suit different activity modes, and the pneumatic part is adjusted mainly to suit different walking speeds. Threshold selection is carried out to distinguish between walking and standing, for example, whereby the output signals from one or both of a load-sensitive sensor and a stroke sensor are stored to define thresholds between the different activity modes. The outputs of both sensors are monitored throughout the walking cycle.

Once all required tests have been performed or, indeed, at a intermediate stage, the teach routine can be exited by selecting an "exit program mode" command at step 150, whereupon the calculations described above in connection with step 130 are performed and the results stored, together with all valve settings and associated load and speed settings. These are written as a complete set of control data to the EEPROM (steps 152 and 154).

Referring back to FIG. 4, exiting the program mode in step 150 of FIG. 5B causes the receiver in the prosthesis to be switched off and the processor circuit 32 enters a playback routine which will be described hereinafter with reference to FIGS. 8 to 10. In essence, the playback routine has the function of monitoring the activity mode of the amputee and, during ambulation, measuring the step period (i.e. walking speed) by analysing the outputs of the two limb-mounted sensors. The pneumatic and hydraulic valves are driven automatically to the optimum settings on the basis of the programmed information obtained during the teach routine.

Before considering the sequence of operations in the playback routine it is appropriate to explain how different activity mode are detected.

Activity mode detection includes calculating for each walking step the integral of the load profile sensed by the force sensing resistor 28 of FIG. 1 with respect to stance time during the stance phase, thereby normalising the integral for walking speed. The measured integral is the integral of the difference between the measured force and a force reference level, when the former exceeds the latter. The normalised integral is calculated immediately after the end of the stance phase, the value being stored as "a ramp mode detection index". If the value exceeds a threshold value of the index set during level walking by a predetermined margin, the ramp descent mode is detected. The force reference level is set at the beginning of each stance phase as being equal to the instantaneous force sensed by the force sensing resistor at the instant when the swing phase ends and the stance phase begins, as defined by the threshold set in the threshold select operation of the teach routine (see step 140, etc. in FIG. 5B). Thus, the ramp descent mode is selected when the current normalised force integral is greater than the maximum normalised level walking force integral plus a ramp margin and a safety offset as shown in FIG. 6-1. Referring to FIG. 6-2, exiting the ramp descent mode is similarly detected when the current normalised force integral is less than the maximum nornalised level walking force integral plus the ramp margin. In fact, the calculated ramp mode detection index is compared with the index calculated in fast, normal, and slow walking and only if it is larger than all of these is the descent ramp mode detected. Sub-modes of the ramp descent mode can be derived in a similar way by setting successively increased index thresholds for a gentle incline, a medium incline and a steep incline, for example.

Figure 3:
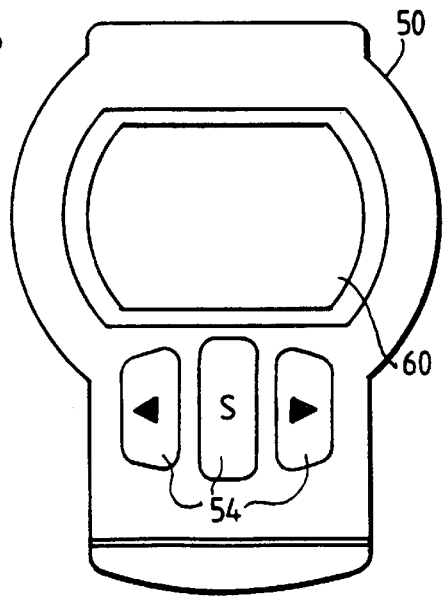
FIG. 3 is a plan view of an operator control unit.

The standing mode is detected by detecting continuous extension of the limb for a period which is programmable during the teach routine to be longer than the maximum period of extension reached during walking or other ambulation modes. The period is typically 2 to 3 seconds, but may be 4 seconds, as shown in FIG. 6-3. A further requirement which may be introduced is the existence of a force sensor reading greater than a loaded limb threshold set during the threshold selection step of the teach routine (typically 0.2 and 0.4 times the load when the whole of the body weight is applied to the extended limb). Referring to FIG. 6-4 the standing mode is exited and the hydraulic lock released if the stroke reading sensed by the magnetoresistive transducer is greater than a standing threshold value of the stroke which may be a relatively small flexion angle in the range 5° to 20°. Alternatively, the standing mode may be exited when the gradient of the force sensor output is greater than ¾ of the same gradient measured during programming when the amputee takes a first step with the natural leg, starting from the standing position.

The sitting mode is detected when the stroke sensor indicates a flexed knee occurring for a period greater than an interval of 2 to 7 seconds, typically 4 seconds, as indicated in FIG. 6-5. This may be coupled with a requirement for a force reading which is less than the loaded limb threshold. Exiting from the sitting mode occurs when the stroke reading is less than an extension threshold, indicating extension of the knee to a point approaching full extension, see FIG. 6-6. In the sitting mode the resistance to flexion is set low.

Figure 7:
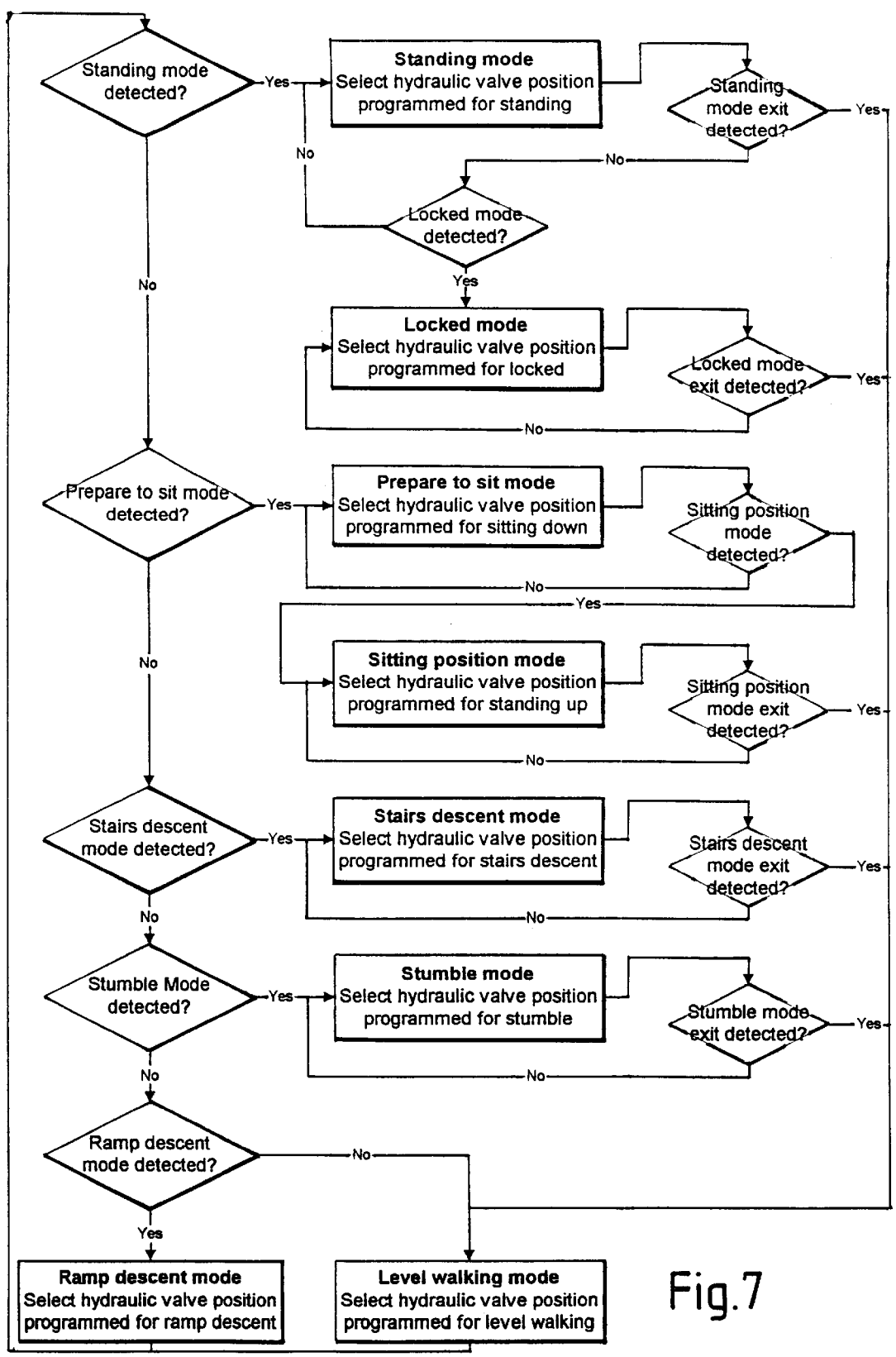

A knee locked mode may be selected and exited voluntarily by the amputee by e.g. repeatedly loading and unloading the limb in a particular sequence, providing the knee is extended, as indicated in FIGS. 6-7 and 6-8. A switch may be used instead, as shown.

A separate mode is provided for descending stairs. This is selected automatically as shown in FIG. 6-9, when (I) the knee flexed period is greater than the maximum flexed period achieved during normal level walking plus an offset value, preferably, and (ii) the flexed period is less than two seconds and (iii) the maximum flexion angle of the knee during one cycle is greater than a preset amount, preferably the minimum value for the peak flexion angle occurring during the swing phase when the amputee is walking normally on a level surface. The stairs descent mode can be exited voluntarily by means of an amputee-operated switch or repeated loading and unloading of the limb when extended, as shown in FIG. 6-10. Alternatively, the stairs descent mode can be exited if the flex period is less than the maximum flexed period achieved during normal level walking.

Referring to FIG. 6-11, the limb enters a stumble mode in two situations. Both situations are qualified by the walking speed being less than the maximum achieved level walking speed so as to eliminate the possibility of running being mistaken for a stumble. The two alternative stumble conditions are (a) that the knee-extended period is less than ¾ the minimum extended period at the immediately preceding walking speed, or (b) the reading from the stroke sensor (i.e. flexion angle) has a positive gradient (increasing angle) immediately after a negative gradient, during the flexed state. Criterion (a) indicates that flexion has occurred much too early (e.g. due to insufficient hip moment being applied by the amputee, leading to a stumble). Criterion (b) detects the situation of, e.g. the amputee catching the foot during the swing phase, thereby interrupting the continuous reducing flexion angle during the latter part of the swing phase. In this way, it is possible to select a stumble mode which locks the knee against flexion even when it is a partly flexed state, to prevent further collapsing and thereby to provide support against a fall. This stumble mode is exited when the stroke sensor reading indicates that the knee is once again in the extended state (FIG. 6-12).

The hydraulic valve position is selected according to the detected mode in a series of consecutive checks as shown by the flowchart of FIG. 7.

Figure 8A:
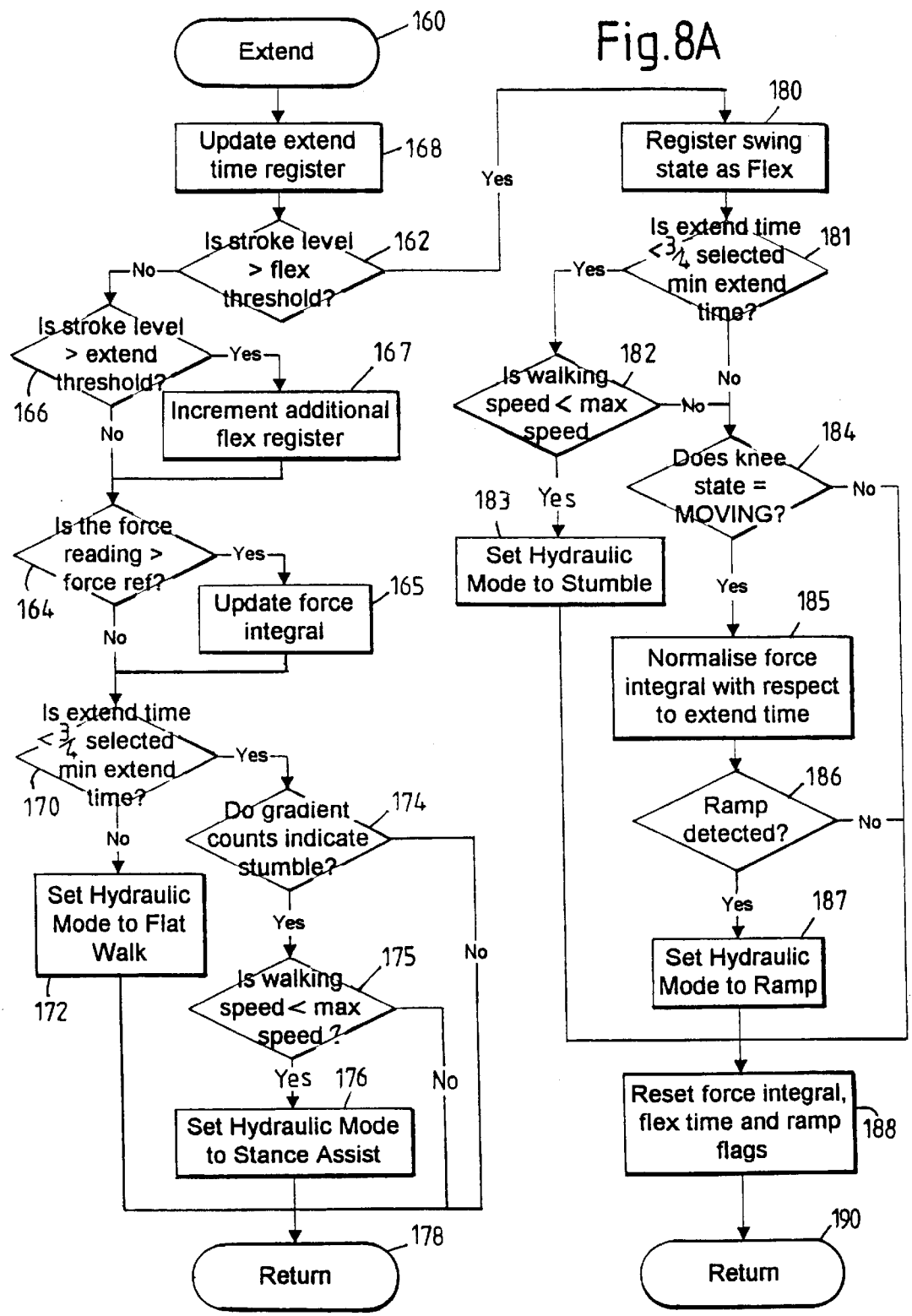

Referring now to FIGS. 8A and 8B, mode detection during the playback routine applied during ambulation is governed by the condition of the knee joint at any given moment, specifically whether the knee joint is extended or flexed. Accordingly, the playback routine is decided into two main states: "Extend" and "Flex". These two states are indicated by the reference numerals 160 and 200 respectively in FIGS. 8A and 8B. The routine can cycle repeatedly in part of the Extend state 160 or in part of the Flex state 200 so that in each of these states the stroke sensor (magnetoresistive transducer 26B in FIG. 1) can be monitored to determine whether a flex threshold or an extend threshold set during the teach routine has been exceeded or not.

During the Extend state 160, each cycle contains steps in which the stance phase stroke and force parameters are measured from the sensors 26A and 28 (steps 162 and 164). Unless the stroke level (representing the flexion angle) is greater than the flex threshold, the first parameter is compared with the force reference value which was set at the beginning of the stance phase. This reference value is obtained by measuring the force sensing resistor output as the knee angle passes the extend threshold, typically in the region of 5° of knee angle or slightly higher. If the measured force is greater than the reference value, the integral for calculating the ramp mode index is incremented in step 165 if the force reading from the force sensing resistor is less than or equal to the stored force reference, the integral is not incremented. Prior to this, the stroke level is also compared with the extend threshold and if it is greater, a so-called "additional flex" is incremented for use as a time measurement in the Flex state (steps 166 and 167).

In the Extend state, an extend time register is updated in each cycle within the Extend state (step 168) and this extend time value compared in step 170 with ¾ of the selected minimum extend time as part of a stumble detecting stage, and referred to above in connection with FIG. 6-11. A negative result of this comparison indicates level walking and the hydraulic mode is set to "flat walk" (step 172). An affirmative result leads to an evaluation of gradient counts indicative of the stroke level gradient described above with reference to FIG. 6-11. This query stage is indicated in FIG. 8A by step 174. The walking speed check of FIG. 6-11 is performed by query stage 175 such that if the measured walking speed is less than the maximum level walking speed, the stumble mode (here indicated in step 176 as "stance assist") is set. Having selected either level walking or stumble/stance assist mode, the routine returns (step 178) to the beginning of the Extend state routine at step 160.

A magnetoresistive sensor output (stroke level) greater than the flex threshold (about 5° flexion angle) breaks the Extend state cycle to register the swing state as a Flex state (step 180). Again, steps are now performed to detect a stumble by comparing the extend period with a fixed weighting of the extend period during walking (here the weighting is ¾) (Step 181). An affirmative result leads to a walking speed check 182 like step 175 which, if affirmative causes the hydraulic mode to be set to stumble or stance assist (step 183). If the extend period detected in step 181 is normal, and the knee angle is changing (step 184), a ramp detection stage is entered, in that the final value of the integral calculated in step 165 can be normalised by dividing the integrated force by the extend period (step 185) and the parameters resulting from the just-ended stance phase are used to detect whether the amputee is walking on a level surface or down an incline (step 186). In the latter case, the hydraulic mode is set to ramp descent mode (step 187).

Whether the mode is level walking, ramp descent, or stumble, the force integral is now reset in step 188, along with resetting of a flex time register and ramp flags. At this point the routine moves into the Flex state (step 190).

Having now passed into Flexed state 200, a new cycling phase begins with updating of the flex time register (step 202).

Next, the stroke level is monitored to check whether it has reached a value predetermined for force reference storing and in the event of an affirmative result, a new force reference is set, equal to the prevailing force level (steps 204 and 205). At this point the stroke level is checked against the extend threshold to determine whether the knee is in the flexed state still, or whether it is moving into the Extend state (step 206). If it is remaining in the Flex state, the routine remains in the cycling part of the Flex state. It often happens that an amputee will not keep the knee in an extended state when standing, but will make repeated or occasional relatively small flexion movements for comfort. Step 207 compares the flexion angle with a 'stand' threshold plus offset, which together may amount to an angle between 5° and 10° If the amputee is standing, a "high flex" flag is set "step 209) to indicate that flexion is occurring in a standing mode, which can be used then to allow transfer to a sitting mode. If the flexion angle is less than the stand threshold (step 208) while the patient is standing, then the flag is cleared (step 210) indicating that the patient is now standing without flexion. These steps (207 to 210) have no effect if the amputee is walking.

At steps 211 and 212, the stroke level or flexion angle is compared with a stored swing valve for the maximum swing angle and, if greater, the swing valve is updated for use as a reference when needed.

As in the Extend state, the stroke sensor gradient counts are monitored according to FIG. 6-11 to detect a stumble (step 213) whereupon the mode remains unchanged or alters to stumble (stance assist) (step 214). At this point the routine returns to the beginning of the flex state (steps 215 and 200). If the stroke level has extended below the extend threshold in step 206, the routine enters a Flex state exiting stage in which the swing state is registered as extend in step 220, the high flex flag referred to above, if set, is cleared (step 222), the additional flex register content (set in step 267 described above) is updated by adding in the current flex period, and the updated value is compared with the maximum level walking flex period plus an offset (steps 224 and 225), representing the beginning of a stairs descent detection stage (described above with reference to FIG. 6-9). If the additional flex value is greater than this level walking flex period plus offset, and the additional flex period is less than 2 seconds (step 226) and, furthermore, the stroke level is greater than the minimum peak swing level for level walking (see FIG. 6-9) (step 227), the hydraulic mode is set to stairs descent (step 228). Otherwise, the mode remains unchanged.

A negative result in step 225 combined with the "additional flex" period being less than the maximum level walking flex period (step 230), or a negative result in step 236, leads to checking a "stairs descent flag" which is set when and one of the three conditions indicated in FIG. 6-10 is satisfied (step 232). A positive result causes an exit from the stairs descent mode (step 233.)

At the conclusion of the stairs descent detection stage, the routine returns once again to the beginning of the Extend state (step 235 to step 160).

Figure 9:
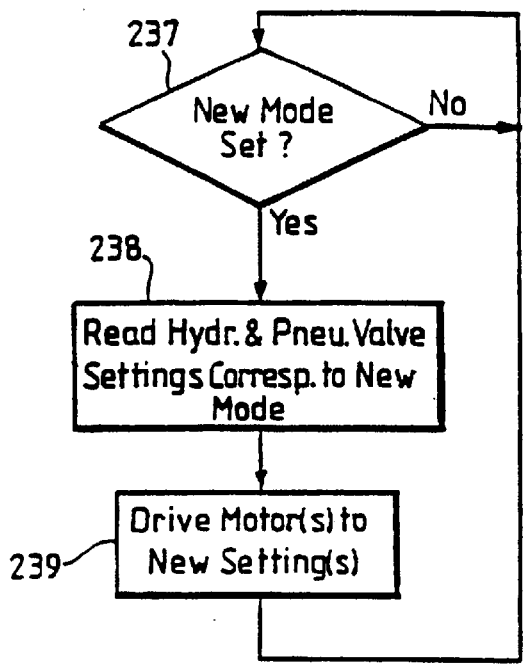
Figure 10:
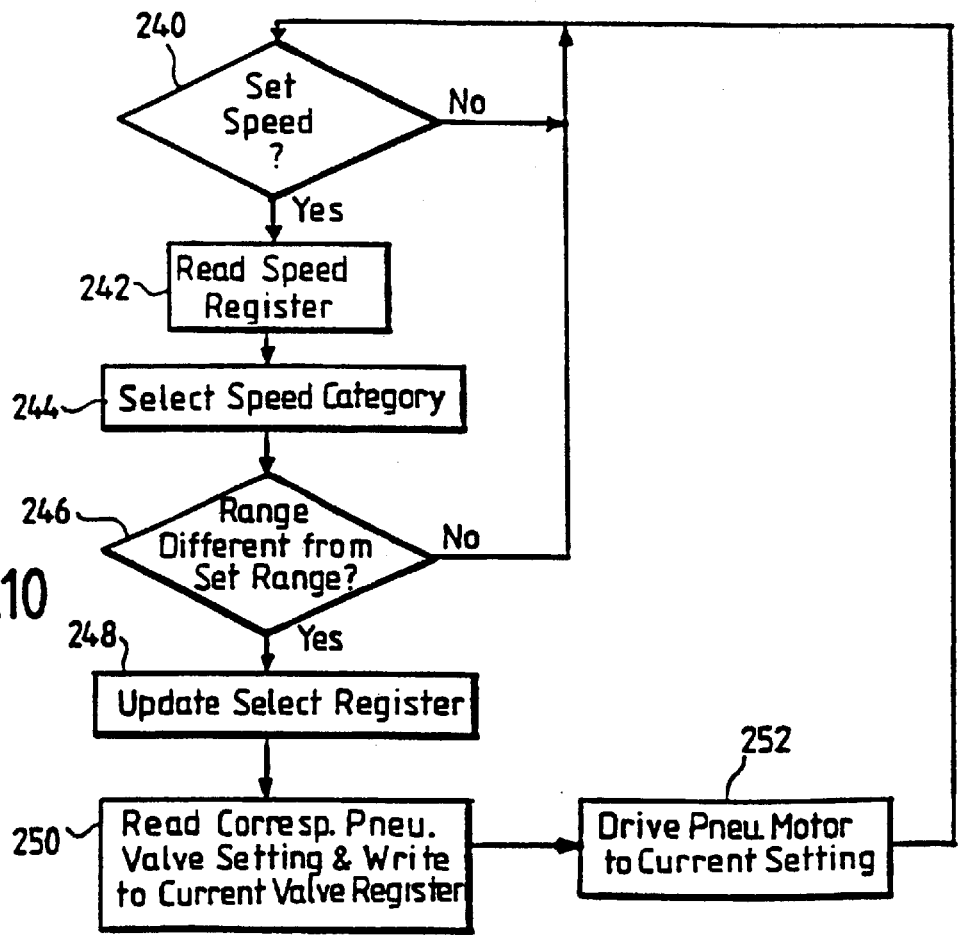

If a new mode is set in the Flex or Extend states, the hydraulic and pneumatic valves 18H and 180 (FIG. 1) are driven to the settings stored in the control data derived from the teach routine, as shown by steps 237, 238, and 239 in FIG. 9. One of the features of the described system is that the setting of the hydraulic valve 18H during each activity mode remains constant (at the programmed setting) until the activity mode changes, thereby avoiding excessive power consumption by the associated monitor.

One of operations performed during ambulation is the processing of stroke sensor readings to obtain a step period reading indicative of the speed of walking. This leads to updating of a speed register set up by the processor, the contents of which register a rapidly responding indication of walking speed during the walking mode. In order to adapt flexion resistance to varying walking speed, a valve setting routine is performed, as illustrated by the flowchart of FIG. 10. Having registered the set speed state at step 240, the routine causes reading of the above-mentioned speed register for the latest step period (step 242) followed by a comparison of the step period with a boundary value of the step period ranges stored in the EEPROM (step 244) to determine whether the indicated step period range is different from the range already set in a selected register (step 246). If no difference is detected, the program links back to the beginning of the routine. However, if a difference is detected, the select register is updated (step 248), the corresponding pneumatic valve setting for the new range is read from the EEPROM store and written to the current valve register (step 250) and the stepper motor for the pneumatic valve is driven to the setting corresponding to the value in the current valve register (step 252).

In summary, the adaptive control system described above makes use of sensors for determination of both kinetic and kinematic parameters at the knee level to adjust a control unit having both hydraulic and pneumatic variable volume chambers in order to control flexion in both the stance phase and the swing phase. The preferred sensors are a force sensing transducer and a displacement or proximity transducer for knee angle monitoring. The former may make use of relatively movable parts of either the thigh component or the shin component of the prosthesis in the region of the knee joint to measure loading on the limb which is a function solely or primarily of the knee bending moment, i.e. the bending moment applied about the axis of rotation of the knee joint during use of the prosthesis. The proximity sensor is preferably the combination of a permanent magnet and a magnetoresistive transducer on relatively moving parts, one associated with the thigh component and the other with the shin component. Signals from the transducers are fed to a microprocessor controller having a remote control receiver which is responsive to command signals from a remote control programming unit. This may be operated by either prosthetist or amputee. The control system is capable of providing automatic swing and stance control at different walking speeds over different terrain, whether level or inclined. The load sensor continuously monitors the applied loads around the knee, whilst the proximity sensor continuously monitors knee swing. A microprocessor analyses the data from the sensors and from the pattern of kinetic and kinematic data individual parameters associated with walking on the flat or on slope are established. The speed of walking is determined from the knee kinematic data The remote control programming unit allows adjustment of hydraulic stance control to suit flat walking, standing, sitting, walking down slopes and descending stairs. Locking of the knee against flexion in a stumble condition is also provided. This is achieved using a motorised valve which adjusts the resistance to movement of hydraulic fluid in a double piston hybrid hydraulic/pneumatic piston and cylinder assembly. Settings for swing control at slow, normal, and fast walking speeds are also allowed by the remote control programming unit which can perform remote adjustment of a motorised pneumatic valve using walking speed boundary levels processed in the limb-mounted microprocessor. The control devices regulate flexion resistance during the stance and swing. Extension terminal impact damping is provided independently of walking speed or terrain and is manually adjustable by a separate hydraulic valve associated with the variable hydraulic chamber. Once programmed for the user, the system monitors kinetic and kinematic parameters of locomotion, and automatically adapts the swing and stance controls to different walking speeds and different activities of the amputee, thereby removing the need for the amputee to make compensatory gait pattern alterations as speed and terrain change.

The above-described prosthesis uses stumble protection techniques which rely on detecting an abnormally short extend period by comparison with the immediately preceding extend period or periods (or a predetermined fraction thereof), or on detecting an interruption in the continuously decreasing flexion angle associated with the swing phase in normal walking.

What is claimed is:

1. A lower limb prosthesis for an above-knee amputee, having an adaptive control system which comprises a knee flexion control device arranged to resist flexion at a knee joint both hydraulically and pneumatically, and an electronic processing circuit electrically coupled to sensor means and a control device for automatically adjusting the hydraulic and pneumatic resistance to knee flexion according to actions of the amputee.

2. A prosthesis according to claim 1, wherein the sensor means is arranged to generate electrical sensor signals in response to loading of the prosthesis, and the control system is arranged such that the knee joint resistance to knee flexion is controlled at least predominantly hydraulically during a stance phase of a walking cycle of the prosthesis.

3. A prosthesis according to claim 2, wherein the control system is arranged such that the resistance to knee flexion is controlled at least predominantly pneumatically during a swing phase of the walking cycle of the prosthesis.

4. A prosthesis according to claim 2, wherein the knee flexion control device comprises a piston and cylinder assembly having a chamber containing hydraulic fluid and a chamber containing gas, wherein the volume of each chamber varies according to the degree of knee flexion, the flow of fluid or gas respectively to or from the chambers being controlled by a plurality of valves controlled in response to setting signals from the processing circuit, and wherein the chamber containing hydraulic fluid has an associated bypass means located so as to be effective only within an upper range of angular knee flexion.

5. A prosthesis according to claim 4, without a mechanical extension spring of stiffness greater than 6 lb/in (0.11 kg/mm).

6. A prosthesis according to claim 4, further comprising a mechanical extension spring.

7. A prosthesis according to claim 6, wherein the mechanical extension spring has stiffness less than or equal to 6 lb./in. (0.11 kg./mm).

8. A prosthesis according to claim 2, wherein the sensor means includes a flexion sensor arranged to provide a sensor signal indicative of the degree of flexion of the knee joint.

9. A prosthesis according to claim 8, wherein the flexion sensor comprises the combination of a magnetoresistive transducer and a magnet respectively mounted on parts of the prosthesis which move relatively to each other as the knee joint is flexed.

10. A prosthesis according to claim 1, wherein the control system is arranged such that the resistance to knee flexion is controlled at least predominantly pneumatically during a swing phase of a walking cycle of the prosthesis.

11. A prosthesis according to claim 1 or claim 2, wherein the control system is configured such that flexion is hydraulically resisted substantially only within an initial part of an angular range of flexion of the knee joint from full extension.

12. A prosthesis according to claim 11, wherein the hydraulic resistance to flexion predominates over an initial angular flexion range of from substantially zero to an upper angular limit which is no greater than 35°.

13. A prosthesis according to claim 12, wherein the upper angular limit is between 30° and 35°.

14. A prosthesis according to claim 11, wherein the knee flexion control device comprises a piston and cylinder assembly having a chamber containing hydraulic fluid, wherein the volume of the chamber varies according to the degree of knee flexion, and wherein the chamber has associated bypass means located such that the resistance to movement of the piston and cylinder assembly due to the hydraulic fluid is insignificant over an upper range of angular knee flexion in comparison with the resistance of the assembly due to the hydraulic fluid within the said initial part of the angular range of flexion from full extension.

15. A prosthesis according to claim 14, wherein the bypass means comprises an enlargement of the cylinder over part of the stroke of the piston.

16. A prosthesis according to claim 1, wherein the control system is configured such that the flexion control device provides pneumatic knee extension assistance and hydraulic terminal extension damping during a swing phase of a walking cycle of the prosthesis.

17. A prosthesis according to claim 1, wherein the knee flexion control device is arranged to resist flexion hydraulically and pneumatically simultaneously during a stance phase of a walking cycle of the prosthesis with the hydraulic resistance predominating such that adjustment of the hydraulic and pneumatic resistance respectively provides for coarse and fine control of flexion resistance.

18. A prosthesis according to claim 1, wherein the sensor means and the processing circuit are operable together to generate a descent control signal indicative of the amputee walking down a slope as opposed to walking on a level surface, and wherein the processing circuit is operable to feed a setting signal to the control device to increase the hydraulic resistance to increasing knee flexion in response to the descent control signal.

19. A prosthesis according to claim 18, wherein the sensor means includes a sensor located at the knee level to provide a sensor output signal indicative of a knee bending moment, the processing circuit being operable to process the sensor output signal to detect the amputee descending a slope and to generate the descent control signal.

20. A prosthesis according to claim 19, wherein the processing circuit is operable to generate a signal representative of an integral of the sensor output signal over a period of time during a stance phase of a walking cycle of the prosthesis and to generate the descent control signal in response to the integral exceeding a predetermined value.

21. A prosthesis according to claim 18, wherein the processing circuit monitors an output signal from the sensor means to detect an increase in the knee bending moment with reference to a predetermined threshold, the increase occurring over a period of time representing a major part of a stance phase of a walking cycle of the prosthesis, thereby to produce the descent control signal.

22. A prosthesis according to claim 1, wherein:
the control device is arranged to resist knee flexion hydraulically during a stance phase of a walking cycle of the prosthesis,
the sensor means are for generating electrical sensor signals in response to loading of the prosthesis, and
the processing circuit is arranged to feed a descent control signal to the control device in response to detection of the amputee descending an incline, the descent control signal causing an increase in the resistance of the control device to knee flexion compared with a resistance set for level walking.

23. A prosthesis according to claim 22, wherein the sensor means comprise a sensor located at the knee level of the prosthesis and arranged to generate a sensor signal which is a function of a bending moment at the knee tending to cause knee flexion.

24. A prosthesis according to claim 23, wherein the processing circuit is arranged to generate the descent control signal as a function of an integral of the sensor signal with respect to time.

25. A prosthesis according to any of claims 22 to 24, wherein the sensor means include a flexion sensor arranged to provide a sensor signal indicative of a degree of flexion of the knee joint.

26. A prosthesis according to claim 1, wherein:
the control device is arranged to resist flexion at the knee joint hydraulically during a stance phase of a walking cycle of the prosthesis,
the sensor means are for generating electrical sensor signals in response to loading of the prosthesis at the knee level, and
the processing circuit is arranged automatically to adjust the resistance to knee flexion in response to changes in the sensor signals occurring when the amputee moves from walking on a level surface to walking down an incline and vice versa.

27. A prosthesis according claim 26, wherein the sensor means are arranged to sense a load on the prosthesis and the degree of flexion, and wherein the processing circuit uses the sensor signals to monitor both of these parameters with respect to a predetermined time period in the order of 3 to 7 seconds to sense a sitting condition and a standing condition.

28. A prosthesis according to claim 26, wherein the processing circuit is arranged automatically to adjust the resistance to flexion in response to changes in the sensor signals occurring when the amputee at least one of sits down, stands up, stops walking and starts walking.

29. A prosthesis according to claim 28, wherein the sensor means are arranged to sense changes in a bending moment applied to the knee.

30. A prosthesis according to claim 26 or claim 28, wherein the sensor means are arranged to sense changes in a bending moment applied to the knee.

31. A prosthesis according to claim 30, wherein the processing circuit is arranged to generate a descent control signal and to feed the descent signal to the knee flexion control device so as to set an increased stance phase resistance to knee flexion when an integral of a bending moment at the knee as sensed by the sensor means and normalized with respect to a step period exceeds a stored threshold value, whereby the resistance to flexion in the stance phase is higher when the amputee is descending a slope than during level walking.

32. A prosthesis according to claim 30, wherein the sensor means comprises a transducer mounted on a structural member of the prosthesis substantially adjacent a pivot axis of the knee.

33. A prosthesis according to claim 32, wherein the structural member comprises a first part and a second part, wherein the first part is a lever arm connected for pivotal movement relative to the other structural member part about an axis substantially parallel to but spaced from the knee axis of rotation, and wherein the transducer is mounted so as to produce a sensor signal representative of the deflection of the lever arm relative to the second structural part.

34. A prosthesis according to claim 33, wherein the processing circuit is arranged to generate a descent control signal and to feed the descent signal to the knee flexion control device so as to set an increased stance phase resistance to knee flexion when an integral of a bending moment at the knee as sensed by the sensor means and normalized with respect to a step period exceeds a stored threshold value, whereby the resistance to flexion in the stance phase is higher when the amputee is descending a slope than during level walking.

35. A prosthesis according to claim 32, wherein the processing circuit is arranged to generate a descent control signal and to feed the descent signal to the knee flexion control device so as to set an increased stance phase resistance to knee flexion when an integral of a bending moment at the knee as sensed by the sensor means and normalized with respect to a step period exceeds a stored threshold value, whereby the resistance to flexion in the stance phase is higher when the amputee is descending a slope than during level walking.

36. A prosthesis according to claim 32, wherein the sensor means comprises a force transducer and the structural member has two parts which move relative to each other according to a load applied to the prosthesis, and wherein the force transducer is mounted to one of the two parts so as to be acted upon by the other part and to produce a sensor signal dependent on the load applied to the prosthesis.

37. A prosthesis according to claim 36, wherein the processing circuit is arranged to generate a descent control signal and to feed the descent signal to the knee flexion control device so as to set an increased stance phase resistance to knee flexion when an integral of a bending moment at the knee as sensed by the sensor means and normalized with respect to a step period exceeds a stored threshold value, whereby the resistance to flexion in the stance phase is higher when the amputee is descending a slope than during level walking.

38. A prosthesis according to claim 36, wherein the structural member is associated with a thigh part of the prosthesis.

39. A prosthesis according to claim 38, wherein the processing circuit is arranged to generate a descent control signal and to feed the descent signal to the knee flexion control device so as to set an increased stance phase resistance to knee flexion when an integral of a bending moment at the knee as sensed by the sensor means and normalized with respect to a step period exceeds a stored threshold value, whereby the resistance to flexion in the stance phase is higher when the amputee is descending a slope than during level walking.

40. A prosthesis according to claim 38, wherein the structural member is associated with the thigh part of the prosthesis and the structural member parts comprise a lever arm and a knee chassis, with the lever arm carrying a stump fixing assembly and the knee chassis pivotally connected to a shin part of the prosthesis, the lever arm being resiliently deflectable relative to the knee chassis.

41. A prosthesis according to claim 40, wherein the processing circuit is arranged to generate a descent control signal and to feed the descent signal to the knee flexion control device so as to set an increased stance phase resistance to knee flexion when an integral of a bending moment at the knee as sensed by the sensor means and normalized with respect to a step period exceeds a stored threshold value, whereby the resistance to flexion in the stance phase is higher when the amputee is descending a slope than during level walking.

42. A prosthesis according to claim 40, further including a resilient buffer between the lever arm and the knee chassis, the transducer comprising a force transducer positioned between the buffer and one of the lever arm and the knee chassis.

43. A prosthesis according to claim 42, wherein the processing circuit is arranged to generate a descent control signal and to feed the descent signal to the knee flexion control device so as to set an increased stance phase resistance to knee flexion when an integral of a bending moment at the knee as sensed by the sensor means and normalized with respect to a step period exceeds a stored threshold value, whereby the resistance to flexion in the stance phase is higher when the amputee is descending a slope than during level walking.

44. A prosthesis according to claim 1, wherein:
the control device comprises a hydraulic control device to resist knee flexion hydraulically during a stance phase of a walking cycle of the prosthesis,
the sensor means generate electrical sensor signals in response to loading of the prosthesis, and
the processing circuit is arranged to feed a descent control signal to the control device in response to detection of the amputee descending an incline, as a function of an integral of a quantity relating to a bending moment applied to the prosthesis over at least a major part of the stance phase.

45. A prosthesis according to claim 44, wherein the processing circuit is arranged to generate a ramp index, where $I = \frac{1}{T}\int_{t0}^{t1} F_z \, dt$ and T is the step period or stance phase duration, $t_0$ and $t_1$ are the start and finish of a measuring period representing at least the major part of the stance phase, and F is a sensed parameter related to the a bending moment, and wherein a descent control signal is generated when I is greater than a stored threshold value.

46. An adaptive control system for a lower limb prosthesis intended for an above-knee amputee, comprising a knee flexion control device for resisting flexion at the knee joint both hydraulically and pneumatically, at least one sensor device for generating electrical sensor signals in response to loading of the prosthesis, and an electronic processing circuit electrically coupled to each of the sensor device and the control device for automatically adjusting the hydraulic and pneumatic resistance to knee flexion according to the actions of the amputee.

47. A system according to claim 46, wherein the processing circuit is operable in a program mode and an automatic operation mode, the control system further comprising a remotely operable control unit allowing programming of the system in the program mode, the control device including control means for incrementally increasing or decreasing a hydraulic flexion resistance in real time during an activity test.

48. A system according to claim 46, wherein said at least one sensor device is arranged to sense forces and/or motions at the knee of the prosthesis, and wherein the processing circuit detects actions of the amputee in response to signals generated by said at least one sensor device.

49. A system according to claim 48, wherein the processing circuit is arranged to detect at least one of descending an incline and a stumble condition.

50. A system according to claim 49, wherein said at least one sensor device comprises a sensor for producing a signal representative of a knee bending moment, and wherein the processing circuit is arranged to produce a descent control signal by recognising a signal pattern from said at least one sensor device occurring during a stance phase of the prosthesis, which pattern is associated with descending an incline.

51. A system according to claim 50, wherein the signal pattern recognition comprises comparing a normalised knee bending moment integral derived over at least a portion of the stance phase with a threshold value.

52. A system according to claim 49, wherein said at least one sensor device comprises a knee flexion angle sensor for producing an electrical signal representative of a flexion angle of the knee, and wherein the processing circuit is arranged to produce a stumble mode signal when the said flexion angle signal is indicative of an abnormally short knee extension period.

53. A system according to claim 49, wherein said at least one sensor device comprises a knee flexion angle sensor for producing an electrical signal representative of a flexion angle of the knee, and wherein the processing circuit is arranged to produce a stumble mode signal when the said flexion angle signal is indicative of a positive knee flexion angle gradient following a negative knee flexion angle gradient during a knee flexed state.

54. A system according to claim 49, wherein said at least one sensor device comprises a knee flexion angle sensor for producing an electrical signal representative of a flexion angle of the knee, and wherein the processing circuit is arranged to produce a stumble mode signal when the said flexion angle signal is indicative of an abnormally increasing flexion angle during a stance phase of the prosthesis.

55. A system according to claim 49, wherein said at least one sensor device comprises a knee flexion angle sensor for producing an electrical signal representative of a flexion angle of the knee, and wherein the processing circuit is arranged to produce a stair descent signal when said flexion angle signal is representative of a higher peak knee flexion and/or a longer knee flexed period than normal during walking.

* * * * *